United States Patent
Son et al.

(10) Patent No.: US 10,470,685 B2
(45) Date of Patent: Nov. 12, 2019

(54) METHOD AND APPARATUS FOR CAPTURING MAGNETIC RESONANCE IMAGE

(71) Applicant: Samsung Electronics Co., Ltd., Suwon-si (KR)

(72) Inventors: Jong-bum Son, Seongnam-si (KR); Seong-deok Lee, Seongnam-si (KR); Jae-mock Yi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1407 days.

(21) Appl. No.: 13/973,395

(22) Filed: Aug. 22, 2013

(65) Prior Publication Data

US 2014/0066746 A1 Mar. 6, 2014

(30) Foreign Application Priority Data

Aug. 22, 2012 (KR) .......................... 10-2012-0091989

(51) Int. Cl.
*A61B 5/055* (2006.01)
*G01R 33/56* (2006.01)
*G01R 33/483* (2006.01)

(52) U.S. Cl.
CPC .......... *A61B 5/055* (2013.01); *G01R 33/5602* (2013.01); *G01R 33/4833* (2013.01)

(58) Field of Classification Search
CPC ............... A61B 5/055; G01R 33/4833; G01R 33/5602; G01R 33/50
See application file for complete search history.

(56) References Cited

U.S. PATENT DOCUMENTS

| 6,144,200 | A | 11/2000 | Epstein et al. |
| 6,310,479 | B1 | 10/2001 | Zhu et al. |
| 7,235,972 | B2 | 6/2007 | Shah et al. |
| 8,008,915 | B2 | 8/2011 | Ookawa |
| 2008/0077008 | A1* | 3/2008 | Moll .................. G01R 33/4835 600/425 |
| 2009/0143666 | A1* | 6/2009 | Edelman ................ A61B 5/055 600/410 |
| 2010/0087730 | A1 | 4/2010 | Yamada et al. |
| 2010/0213938 | A1 | 8/2010 | Jeong et al. |

(Continued)

FOREIGN PATENT DOCUMENTS

| JP | 3921369 B2 | 5/2007 |
| JP | 2009-34485 A | 2/2009 |

(Continued)

OTHER PUBLICATIONS

Korean Office Action dated Sep. 5, 2018 in Korean Patent Application No. 10-2012-0091989 (4 pages in English, 5 pages in Korean).

*Primary Examiner* — Rishi R Patel
(74) *Attorney, Agent, or Firm* — NSIP Law

(57) ABSTRACT

A method and apparatus for capturing a magnetic resonance image in which processes of generating T1 contrast for different regions of an object overlap with each other, thereby obtaining a magnetic resonance image having an improved contrast between different tissues within a short time. Therefore, a time required for obtaining a magnetic resonance image may be reduced, and a magnetic resonance image enabling improved diagnosis of a disease or other abnormal condition may be provided.

19 Claims, 6 Drawing Sheets

(56) References Cited

U.S. PATENT DOCUMENTS

| | | | |
|---|---|---|---|
| 2010/0268061 A1 | 10/2010 | Porter et al. | |
| 2010/0277172 A1 | 11/2010 | Takizawa | |
| 2011/0181280 A1 | 7/2011 | Weng | |
| 2011/0181285 A1* | 7/2011 | Greiser | A61B 5/055 324/309 |
| 2011/0263970 A1* | 10/2011 | Xu | A61B 5/055 600/419 |
| 2013/0342206 A1* | 12/2013 | Ugurbil | G01R 33/4835 324/309 |

FOREIGN PATENT DOCUMENTS

| | | |
|---|---|---|
| JP | 4435488 B2 | 3/2010 |
| JP | 2010-148686 A | 7/2010 |
| JP | 4771490 B2 | 9/2011 |
| KR | 1998-031952 A | 7/1998 |
| KR | 10-0671092 B1 | 1/2007 |
| KR | 10-0852402 B1 | 8/2008 |
| WO | WO 90/13047 A1 | 11/1990 |
| WO | WO 2012/088060 A1 | 6/2012 |

\* cited by examiner

METHOD AND APPARATUS FOR CAPTURING MAGNETIC RESONANCE IMAGE

CROSS-REFERENCE TO RELATED APPLICATIONS

This application claims the benefit of Korean Patent Application No. 10-2012-0091989 filed on Aug. 22, 2012, in the Korean Intellectual Property Office, the disclosure of which is incorporated herein by reference in its entirety for all purposes.

BACKGROUND

1. Field

The following description relates to a method and an apparatus for capturing a magnetic resonance image in which processes of generating T1 contrast for different regions of an object overlap each other, thereby obtaining a magnetic resonance image that improves the contrast between different tissues within a short time.

2. Description of Related Art

Magnetic resonance imaging (MRI) forms an image based on information obtained by nuclear magnetic resonance occurring after exposure of an atomic nucleus to a magnetic field. Resonance of the atomic nucleus refers to a phenomenon in which if a particular high frequency energy is incident on the atomic nucleus while it is magnetized by an external magnetic field, the atomic nucleus in a low-energy state absorbs the high-frequency energy and thus is excited to a high-energy state. The atomic nucleus has different resonance frequencies according to its type, and resonance is affected by the strength of the external magnetic field. In the human body, numerous atomic nuclei exhibiting nuclear magnetic resonance exist, and a hydrogen atomic nucleus is generally used to capture a magnetic resonance image.

Recently, techniques for capturing a magnetic resonance image within a short time have been studied. For example, echo-planar imaging (EPI) is one technique that has been studied.

SUMMARY

In one general aspect, a method of capturing a magnetic resonance image includes generating T1 contrast for a first region of an object composed of different tissues; and generating T1 contrast for a second region of the object; wherein the generating of T1 contrast for the first region and the generating of T1 contrast for the second region overlap with each other.

The generating of T1 contrast for the second region may start during the generating of T1 contrast for the first region.

The method may further include obtaining a magnetic resonance signal from the first region by applying a pulse sequence to the first region; and obtaining a magnetic resonance signal from the second region by applying a pulse sequence to the second region.

The obtaining of the magnetic resonance signal from the first region by applying the pulse sequence to the first region may start during the generating of T1 contrast for the second region.

The obtaining of the magnetic resonance signal from the second region by applying the pulse sequence to the second region may start upon completion of the obtaining of the magnetic resonance signal from the first region by applying the pulse sequence to the first region.

The generating of T1 contrast for the second region may start after a time delay corresponding to a repetition time (TR) interval from a start of the generating of T1 contrast for the first region.

The method may further include generating T1 contrast for a third region of the object; wherein the generating of T1 contrast for the second region and the generating of T1 contrast for the third region may overlap with each other.

The method may further include obtaining a magnetic resonance signal from the first region by applying a pulse sequence to the first region; obtaining a magnetic resonance signal from the second region by applying a pulse sequence to the second region; and obtaining a magnetic resonance signal from the third region by applying a pulse sequence to the third region.

The first region and the second region may be different cross-sections of the object.

The first region and the second region may be different subvolumes of the object.

In another general aspect, a non-transitory computer-readable storage medium stores a program for controlling a computer to control an apparatus for capturing a magnetic resonance image to perform the method described above.

In another general aspect, an apparatus for capturing a magnetic resonance image includes a radio-frequency (RF) coil portion configured to apply an RF pulse for generating T1 contrast to a first region of an object composed of different tissues and a second region of the object; and a control unit configured to determine a time point at which the RF pulse is applied to the first region and a time point at which the RF pulse is applied to the second region so that the generating of T1 contrast for the first region and the generating of T1 contrast for the second region overlap with each other.

The control unit may be further configured to determine a time point at which the RF pulse for generating T1 contrast is applied to the second region to be a time point during the generating of T1 contrast for the first region.

The RF coil portion may be further configured to apply a pulse sequence for obtaining a magnetic resonance signal to the first region and the second region; and the apparatus may further include a signal obtaining unit configured to obtain a magnetic resonance signal from the first region in response to the pulse sequence applied to the first region, and a magnetic resonance signal from the second region in response to the pulse sequence applied to the second region.

The control unit may be further configured to determine a time point at which the pulse sequence for obtaining the magnetic resonance signal is applied to the first region to be a time point during the generating T1 contrast for the second region.

The control unit may be further configured to determine a time point at which the pulse sequence for obtaining the magnetic resonance signal is applied to the second region to be a time point following the obtaining of the magnetic resonance signal from the first region.

The control unit may be further configured to determine a time point at which the RF pulse for generating T1 contrast is applied to the second region to be a time point delayed by a time corresponding to a repetition time (TR) interval from a time point at which the RF pulse for generating T1 contrast is applied to the first region.

The RF coil portion may be further configured to apply the RF pulse for generating T1 contrast to a third region of the object.

The RF coil portion may be further configured to apply a pulse sequence for obtaining a magnetic resonance signal to the first region, the second region, and the third region; and the apparatus may further include a signal obtaining unit configured to obtain a magnetic resonance signal from the first region in response to the pulse sequence applied to the first region, a magnetic resonance signal from the second region in response to the pulse sequence applied to the second region, and a magnetic resonance signal from the third region in response to the pulse sequence applied to the third region.

The first region and the second region may be different cross-sections of the object.

The first region and the second region may be different subvolumes of the object.

In another general aspect, a method of capturing a magnetic resonance image includes generating T1 contrast for a plurality of regions of an object; and obtaining a magnetic resonance signal from each of the regions by applying a pulse sequence to each of the regions; wherein the generating of T1 contrast for at least two of the regions is started before starting the obtaining of the magnetic resonance signal from any of the regions.

The generating of T1 contrast for each of the regions may overlap with the generating of T1 contrast for at least one other one of the regions.

The generating of T1 contrast for all of the regions may be started before starting the obtaining of the magnetic resonance signal from any of the regions.

Other features and aspects will be apparent from the following detailed description, the drawings, and the claims.

DETAILED DESCRIPTION

Figure 1:
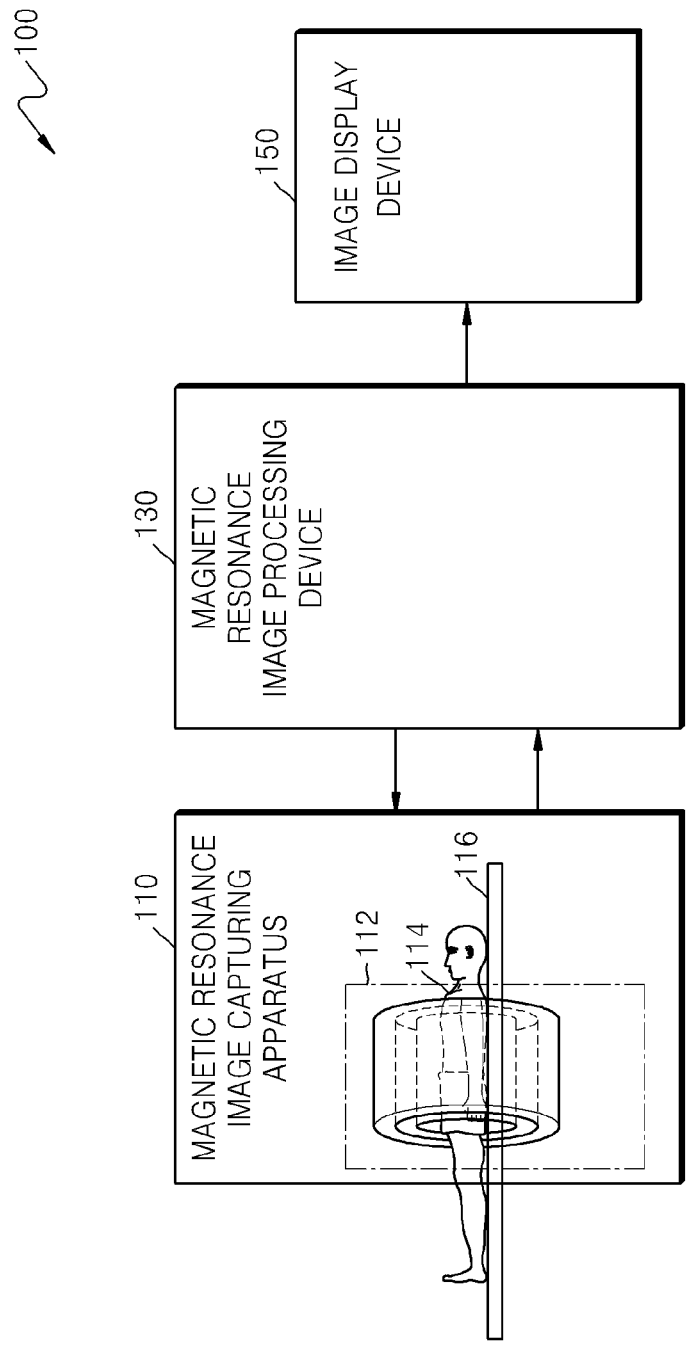
FIG. 1 is a structural diagram showing an example of the entire structure of a magnetic resonance imaging system.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The following description relates to a method and an apparatus for capturing a magnetic resonant image, and any features that are well known to one of ordinary skill in the art will not be described in detail. Atoms exhibiting a nuclear magnetic resonance phenomenon include $^{1}$H, $^{23}$Na, $^{31}$P, and $^{13}$C, among which the hydrogen atom $^{1}$H is mainly used for capturing a magnetic resonance image. Accordingly, in the following description, imaging of the hydrogen atom $^{1}$H will be used as an example.

FIG. 1 is a structural diagram showing an example of the entire structure of a magnetic resonance imaging system 100. The magnetic resonance imaging system 100 includes a magnetic resonance image capturing apparatus 110, a magnetic resonance image processing device 130, and an image display device 150. The components of the magnetic resonance imaging system 100 may be physically integrated rather than being separated as shown in FIG. 1. The magnetic resonance imaging system 100 may be a hybrid magnetic resonance imaging system that is combined with another medical imaging device, such as a positron emission tomography (PET) apparatus.

The magnetic resonance image capturing apparatus 110 receives a control signal for capturing a magnetic resonance image from the magnetic resonance image processing device 130, operates using the control signal, obtains a magnetic resonance signal used to generate the magnetic resonance image from an object 114 positioned on a cradle 116 in a magnet system 112, and outputs the magnetic resonance signal to the magnetic resonance image processing device 130.

The magnetic resonance image processing device 130 receives the magnetic resonance signal from the magnetic resonance image capturing apparatus 110, reconstructs the magnetic resonance image of the object 114 from the received magnetic resonance signal, and transmits the magnetic resonance image to the image display device 150. The magnetic resonance image processing device 130 may include a user interface for receiving control information, etc., from a user, an image processor for reconstructing the magnetic resonance image from the magnetic resonance signal, a storage for storing the magnetic resonance image and various information, and an input and output unit for connection with the magnetic resonance image capturing apparatus 110 and the image display device 150.

The image display device 150 receives the magnetic resonance image reconstructed by the magnetic resonance image processing device 130 and displays the magnetic resonance image on a display unit.

Figure 2:
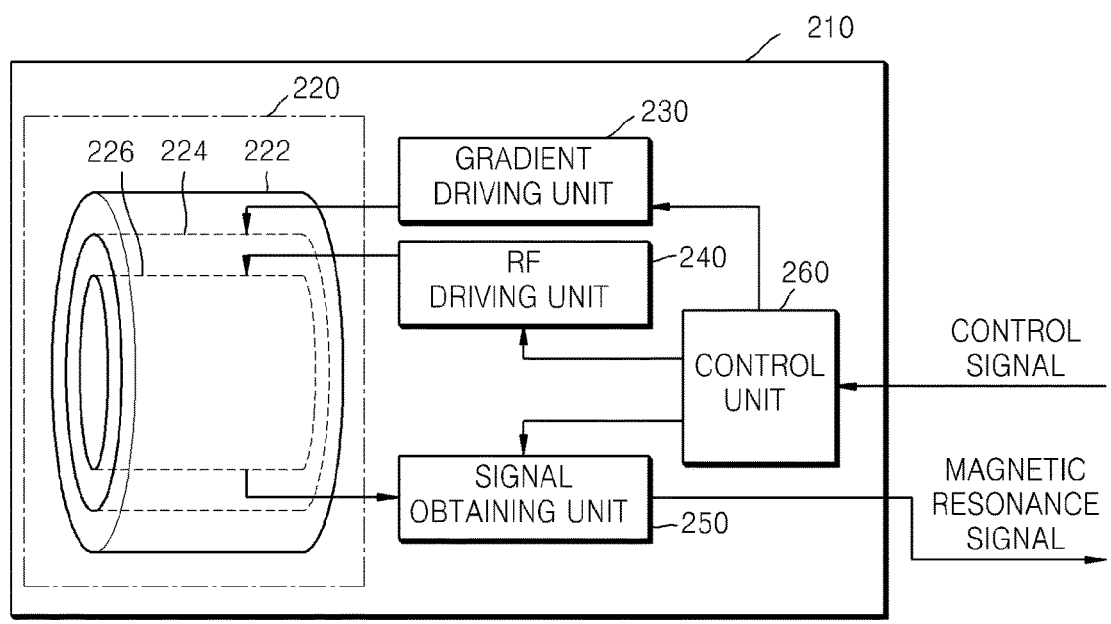
FIG. 2 is a diagram showing an example of a magnetic resonance image capturing apparatus for obtaining a magnetic resonance signal in a magnetic resonance imaging system.

FIG. 2 is a diagram showing an example of a magnetic resonance image capturing apparatus 210 for obtaining a magnetic resonance signal in a magnetic resonance imaging system. The magnetic resonance image capturing apparatus 210 applies a magnetic field and a high frequency signal to an object and obtains a signal sensed from the object in response thereto. The magnetic resonance image capturing apparatus 210 includes a magnet system 220, a gradient driving unit 230, a radio-frequency (RF) driving unit 240, a signal obtaining unit 250, and a control unit 260. The magnet system 220 includes a main magnetic field coil portion 222, a gradient coil portion 224, and an RF coil portion 226.

The main magnetic field coil portion 222 forms a static magnetic field in an internal space of the magnet system 220.

The gradient coil portion 224 forms a gradient magnetic field along three axes that are perpendicular to one another. The three axes are a slice axis, a frequency axis, and a phase axis. When three coordinate axes that are perpendicular to one another in an internal space having a static magnetic field formed therein are x, y, and z axes, any one of the x, y, and z axes may be a slice axis. One of the remaining two axes is a frequency axis, and the other one of the remaining two axes is a phase axis. The slice axis may be slanted at a particular angle with respect to a body axis, i.e., a longitudinal axis, of an object positioned in the magnet system 220, such as the object 114 in FIG. 1.

The gradient coil portion 224 applies three types of gradients in the x-axis, y-axis, and z-axis directions of the object. As a precondition for selectively exciting a particular cross-section perpendicular to the body axis of the object, a gradient magnetic field is formed along the body axis of the object in which a slice selection gradient is applied. To obtain two-dimensional (2D) spatial information on a selected plane, a frequency encoding (FE) gradient and a phase encoding (PE) gradient are applied. As such, to form a gradient magnetic field along the slice axis, the frequency axis, and the phase axis, the gradient coil portion 224 has three types of gradient coils.

The RF coil portion 226 applies an RF pulse for exciting a hydrogen atomic nucleus in the object. The RF coil portion 226 also receives an electromagnetic signal generated as the excited hydrogen atomic nucleus returns to a stable state. The received electromagnetic signal is called a magnetic resonance signal. The RF coil portion 226 may apply various types of RF pulses to the object, and may apply a pulse sequence composed of a plurality of RF pulses to the object.

The gradient driving unit 230 is connected to the gradient coil portion 224, and outputs a signal related to formation of a gradient magnetic field to the gradient coil portion 224. The gradient driving unit 230 includes a gradient driving circuit corresponding to each of the three types of gradient coils with respect to the slice axis, the frequency axis, and the phase axis. The RF driving unit 240 is connected to the RF coil portion 226, and outputs a signal related to application of an RF pulse or a pulse sequence to the RF coil portion 226.

The signal obtaining unit 250 is connected to the RF coil portion 226 and receives the magnetic resonance signal received by the RF coil portion 226 to process the magnetic resonance signal into digital data. The signal obtaining unit 250 may be implemented with an amplifier for amplifying the received magnetic resonance signal, a demodulator for demodulating the amplified magnetic resonance signal, and an Analog-to-Digital Converter (ADC) for converting the demodulated analog signal into a digital format, and may include a storage capable of storing the magnetic resonance signal converted into the digital format. The magnetic resonance signal converted into the digital format is transmitted to the magnetic resonance image processing device 130.

The control unit 260 controls the gradient driving unit 230, the RF driving unit 240, and the signal obtaining unit 250 to obtain the magnetic resonance signal. The control unit 260 receives a control signal transmitted from the magnetic resonance image processing device 130 and controls the magnetic resonance image capturing apparatus 210 by using the received control signal. The control unit 260 may include a memory that may store programs related to operations of the control unit 260, and various data related to application of RF pulses and pulse sequences.

Figure 3:
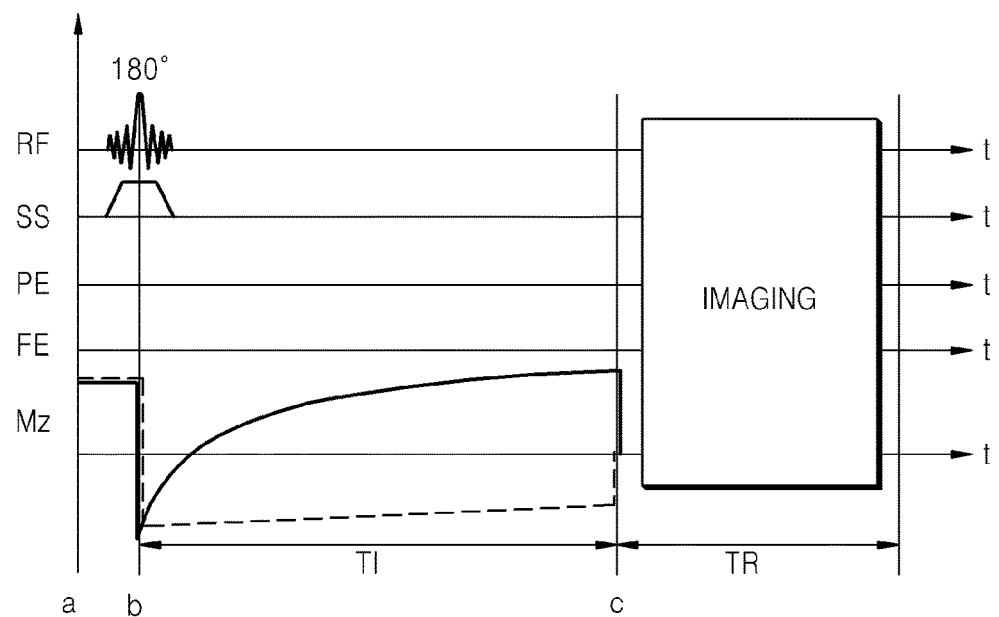
FIG. 3 is a diagram showing an example of a pulse sequence for obtaining a T1 image in a technique for capturing a magnetic resonance image within a short time.

FIG. 3 is a diagram showing an example of a pulse sequence for obtaining a T1 image in a technique for capturing a magnetic resonance image within a short time. The diagram of FIG. 3 shows operating signals for the RF coil portion 226 and the gradient coil portion 224. On the vertical axis, 'RF' denotes a radio-frequency signal applied by the RF coil portion 226; 'SS' denotes a slice selection (SS) gradient applied by the gradient coil portion 224; 'PE' denotes a phase encoding (PE) gradient applied by the gradient coil portion 224; and 'FE' a frequency encoding (FE) gradient applied by the gradient coil portion 224. The horizontal axis indicates time, in which 'TI' denotes inversion time and 'TR' denotes repetition time. 'Mz' denotes magnetization, and in the graph, Mz indicates a magnetization direction of hydrogen atomic nuclei in two different tissues of a region of the object. The solid line in FIG. 3 indicates Mz for one tissue, and the dashed line in FIG. 3 indicates Mz for another tissue. Herein, magnetization denotes net magnetization, which refers to a sum vector of magnetic moments of hydrogen atomic nuclei included in each tissue of the object.

In a magnetic resonance image, a signal is obtained in a frequency domain of the image. In particular, echo-planar imaging (EPI), which is a magnetic resonance image imaging method, minimizes the time of scanning a signal in the frequency domain, thereby allowing an image to be obtained rapidly. However, as a result of obtaining an image rapidly, EPI is limited to imaging a T2 or T2* image feature due to the nature of the imaging method. Therefore, to obtain a T1 image in a technique for capturing a magnetic resonance image within a short time, a process of generating a T1 feature to obtain T1 contrast is additionally necessary as a pre-processing process with respect to an imaging process. In this regard, a detailed description will be provided below with reference to FIG. 3.

At a time point 'a' in FIG. 3, the object is situated in a static magnetic field formed by the main magnetic field coil portion 222. By the static magnetic field, the magnetization directions of hydrogen atomic nuclei in two different tissues of the object are aligned with the direction of the static magnetic field. In FIG. 3, the solid line and the dashed line indicating Mz for two different tissues are in the same direction.

At a time point 'b' in FIG. 3, the RF coil portion 226 applies an RF pulse to the object. This step is an initial step for generating a T1 feature with respect to a particular region of the object. In the object, a gradient magnetic field is already formed in the z-axis direction, and the frequency band of the RF pulse is proportional to the strength of a gradient magnetic field formed in a particular region of the object, which corresponds to a region of interest. The RF pulse includes frequency bands of resonance frequencies hydrogen atomic nuclei have in respective tissues. The RF pulse may be a 180° RF pulse as shown in FIG. 3, and may have various forms, such as a sinc function in a time domain.

After the time point 'b', the RF pulse is cut off, and due to an influence of the static magnetic field already formed in the object, the magnetic moments of the hydrogen atomic nuclei in the tissues of the object are relaxed. The relaxation of the magnetic moments refers to a process in which the hydrogen atomic nuclei excited by the RF pulse are restored to a stable state in the direction of the static magnetic field.

In this process, due to a difference in spin lattice relaxation time between the hydrogen atomic nuclei in the two tissues, in other words, a T1 relaxation time difference, a time taken for the magnetic moment direction of the hydrogen atomic nucleus to be restored to a state before RF pulse application or the restoration speed differs. As a result, an angle between the magnetic moment directions of the hydrogen atomic nuclei in the respective tissues, or from the whole standpoint, an angle between the magnetization directions of the hydrogen atomic nuclei in the respective tissues, gradually increases over time. This means that contrast between T1 features of the respective tissues in a particular region of the object is being generated. Referring to FIG. 3, as indicated by the solid line, an Mz value of one tissue changes from negative (−) to positive (+) within a short time, and after a time TI, the Mz value is restored to a level corresponding to a state before RF pulse application. On the other hand, as indicated by the dashed line, the Mz value of another tissue does not change much, and even after the time TI, the Mz value is not restored to the level corresponding to the state before RF pulse application. As a result, the magnetic moment direction in one tissue is restored to the static magnetic field direction as in the state before RF pulse application as indicated by the solid line, but as indicated by the dashed line, the magnetic moment direction of the other tissue does not change much from the magnetic moment direction in the state before RF pulse application.

At a time point 'c', the magnetic moment directions of the hydrogen atomic nuclei in the two tissues of the object, or from the whole standpoint, the magnetization directions of the hydrogen atomic nuclei in the respective tissues, are oriented opposite to each other. Referring to FIG. 3, the solid line is oriented along a +z axis as at the time point 'a', and the dashed line is oriented along a −z axis as at the time point 'b'. As a result, since the two magnetic moment directions are opposite to each other, an angle between the magnetic moment directions is about 180°. This means that generation of contrast between T1 features of the respective tissues in a particular region of the object is completed.

From the time point 'a' to the time point 'c', in other words, through application of the RF pulse and relaxation of the magnetic moments, the magnetic moment directions of hydrogen atomic nuclei in two tissues of the object, or from the whole standpoint, the magnetization directions of hydrogen atomic nuclei in the respective tissues, become opposite to each other, such that generation of T1 contrast according to the T1 features of the respective tissues is completed. Consequently, a portion for generating T1 contrast is added to the imaging process, and referring to FIG. 3, a time corresponding to TI is added to the imaging time.

From the time point 'c', the RF coil portion 226 starts applying a pulse sequence used to obtain a magnetic resonance signal to the object for imaging. As the pulse sequence, a spin echo pulse sequence may be used, but various pulse sequences, such as a gradient echo pulse sequence and other known pulse sequences, may also be used.

Figure 4:
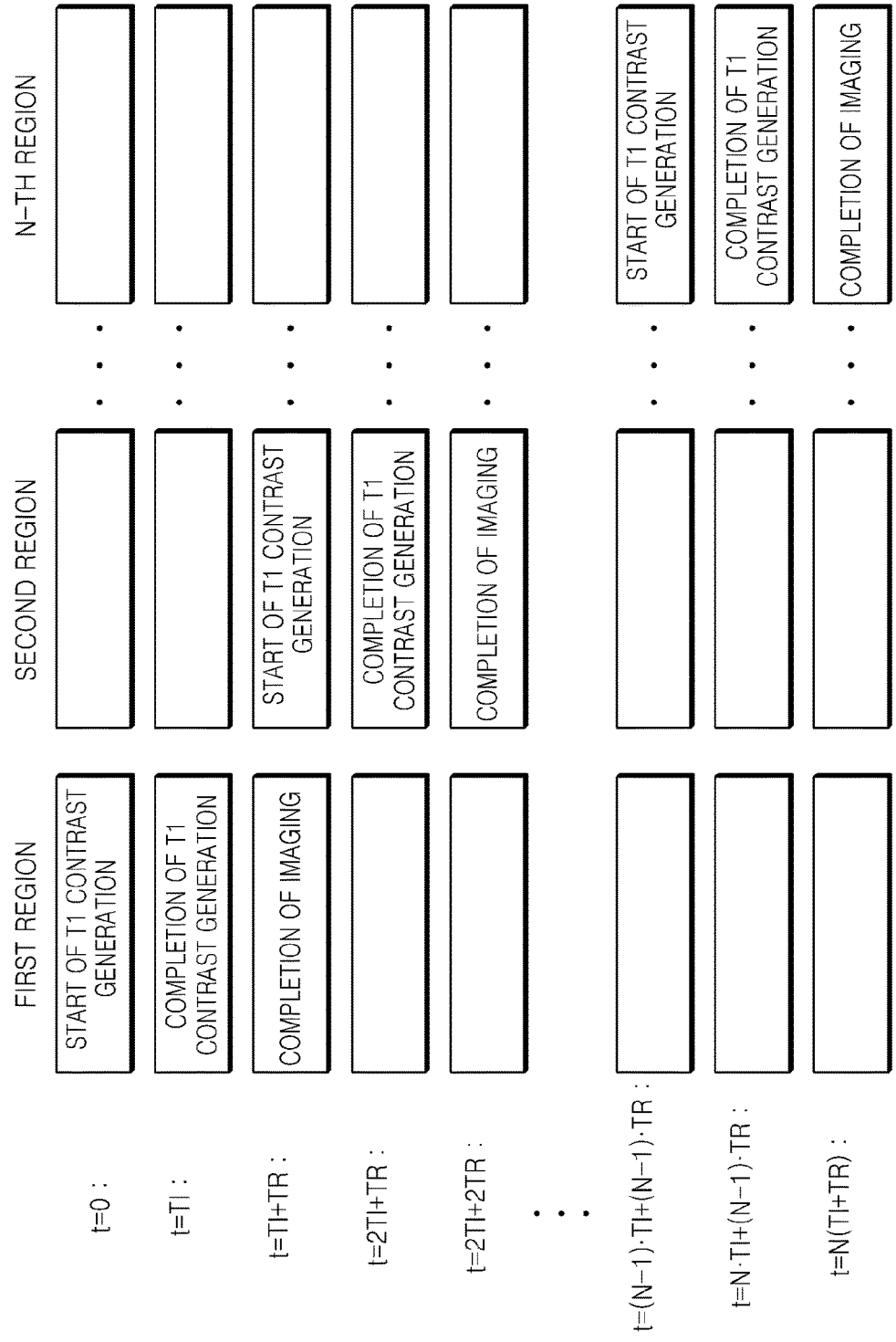
FIG. 4 is a diagram showing an example of a process of obtaining T1 images with respect to a plurality of regions of an object in a technique for capturing a magnetic resonance image within a short time.

FIG. 4 is a diagram showing an example of a process of obtaining T1 images with respect to a plurality of regions of an object in a technique for capturing a magnetic resonance image within a short time. In the foregoing description with reference to FIG. 3, in a technique for capturing a magnetic resonance image within a short time, a portion for generating T1 contrast is added to obtain a T1 image, and a time corresponding to T1 is added to the imaging time. Obtaining images with respect to a plurality of regions of an object will be described below.

FIG. 4 shows a time consumed when an object is divided into a plurality of regions including first through N-th regions to be imaged and a T1 image is obtained for each region using a technique for capturing a magnetic resonance image within a short time. The plurality of regions including the first through N-th regions may be different cross-sections of the object, or may be different subvolumes of the object.

For the first region, at a time t=0, T1 contrast generation starts, and at t=T1, T1 contrast generation is completed. Upon the elapse of TR consumed for imaging after TI, the process of obtaining a T1 image for the first region is completed. That is, to obtain the T1 image for the first region, TI and TR have to pass.

For the second region, the time consumed to obtain the T1 image for the second region is the same as the time consumed to obtain the T1 image for the first region. That is, to obtain the T1 image for the second region, TI and TR have to pass.

Consequently, it can be seen that to obtain the T1 image for up to the N-th image, a scan time expressed by the following Equation 1 is required.

$$\text{Scan Time}=(TI+TR)N \quad (1)$$

As a result, TI, which is a time for generating a T1 feature, increases by as much as the number of regions to be imaged, thus increasing a scan time. For example, in brain imaging, it is important to secure T1 contrast between gray matter (T1=920 ms at 1.5 T) and white matter (T1=780 ms at 1.5 T), and if TI for this end is about 1 second, and TR for imaging of each region is about 100 milliseconds, then a total scan time for obtaining 10 images is about 11 seconds. Thus, since an additional TI for each region is consumed to obtain a T1 image in a rapid imaging technique, such as EPI, application and utilization scopes of the technique for capturing a magnetic resonance image within a short time are limited. To obtain maximum contrast between two tissues of each region, a fixed TI predetermined by a T1 relaxation time needs to be used, such that the TI cannot be reduced arbitrarily. Therefore, to obtain a T1 image in a technique for capturing a magnetic resonance image within a short time, a scheme for minimizing a time consumed in T1 contrast generation is necessary.

Figure 5:
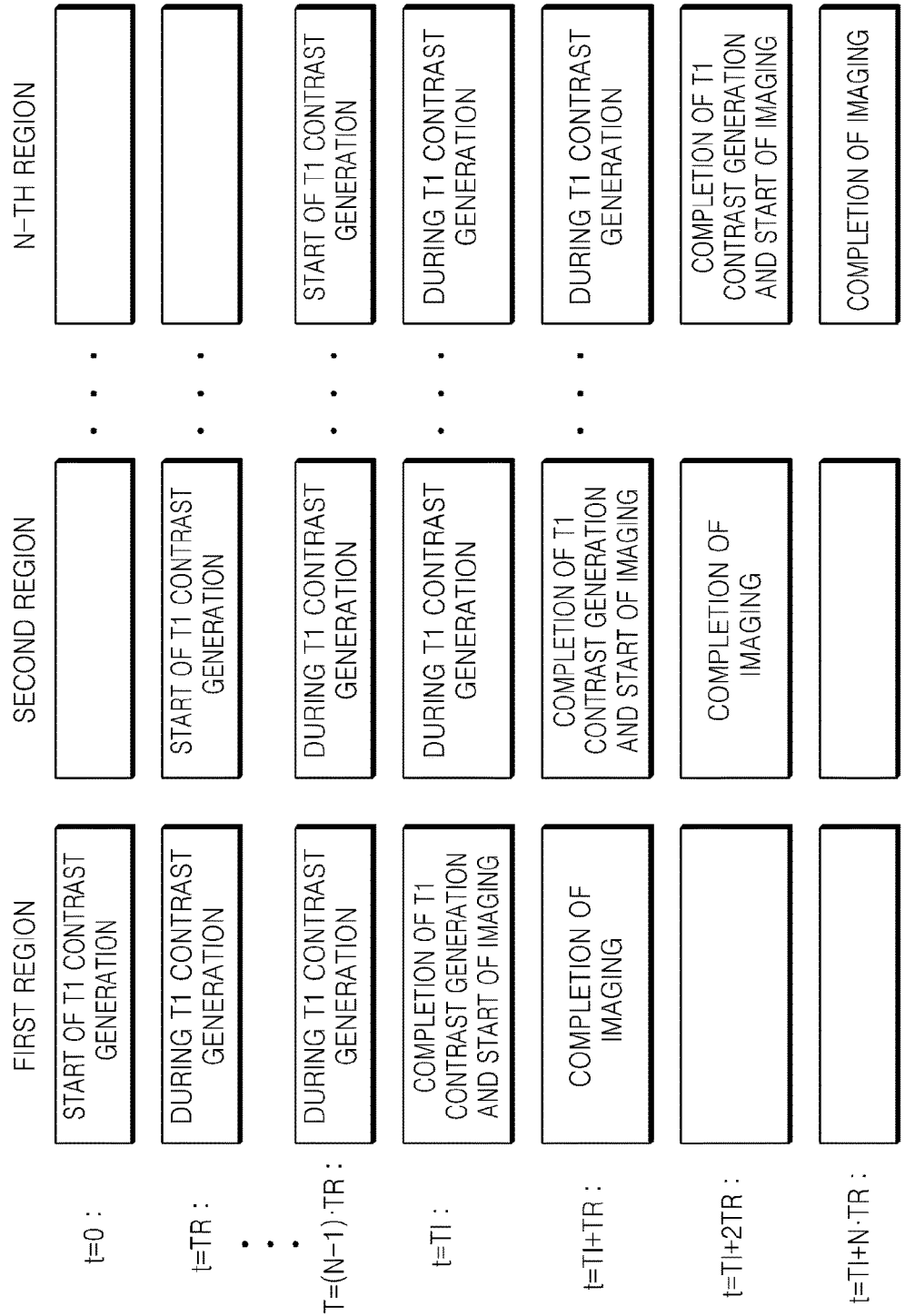
FIG. 5 is a diagram showing an example of a process of obtaining T1 images with respect to a plurality of regions of an object in a technique for capturing a magnetic resonance image within a shorter time than in the example of FIG. 4.

FIG. 5 is a diagram showing an example of a process of obtaining T1 images with respect to a plurality of regions of an object in a technique for capturing a magnetic resonance image within a shorter time than in the example of FIG. 4.

FIG. 5, like FIG. 4, shows a time consumed when an object is divided into a plurality of regions including first through N-th regions to be imaged and a T1 image is obtained for each region using a technique for capturing a magnetic resonance image within a short time. The plurality of regions including the first through N-th regions may be different cross-sections of the object, or may be different subvolumes of the object. The following description is based on a comparison with the process of obtaining the T1 images with respect to the plurality of regions of the object described in FIG. 4.

In FIG. 5, for the first region, at t=0, T1 contrast generation starts, and at t=T1, T1 contrast generation is completed. Upon the elapse of TR consumed for imaging after TI, the process of obtaining a T1 image for the first region is completed. Therefore, comparing FIG. 5 with FIG. 4 for the first region, the time consumed in FIG. 5 is equal to the time consumed in FIG. 4, that is, a sum of TI and TR.

A difference in the process of obtaining T1 images with respect to the plurality of regions of the object is shown beginning from the process of obtaining the T1 image with respect to the second image. For the second region of FIG. 4, T1 contrast generation starts after completion of imaging for the first region, that is, after the elapse of TI and TR; whereas for the second region of FIG. 5, T1 contrast generation starts before the elapse of TI for the first region. In FIG. 5, T1 contrast generation for the second region starts at t=TR before the elapse of TI for the first region, but is not limited thereto. A time consumed to obtain the T1 image for the second region is equal to a time consumed to obtain the T1 image for the first region in FIG. 5, but it should be noted that a start point of T1 contrast generation to obtain the T1 image for the second region in FIG. 5 occurs during T1 contrast generation for the first region. As a result, in FIG. 5, unlike in FIG. 4, generation of the T1 image for the first region and generation of the T1 image for the second region overlap each other. That is, the start point of T1 contrast generation for the second region in FIG. 5 occurs during T1 contrast generation for the first region, rather than occurring after completion of T1 imaging for the first region as in FIG. 4.

Likewise, a start point of T1 contrast generation for the N-th region in FIG. 5 occurs during T1 contrast generation for an (N−1)-th region, such that T1 contrast generation for the N-th region and T1 contrast generation for the (N−1)-th region partially overlap each other.

Consequently, the process of obtaining T1 images with respect to a plurality of regions of an object shown in FIG. 5 requires a scan time expressed by the following equation to obtain the T1 images with respect to the first through N-th regions.

$$\text{Scan Time} = TI + TR \times N \quad (2)$$

That is, in the example in FIG. 5, instead of sequentially obtaining T1 images with respect to respective regions of the object as in the example in FIG. 4, T1 contrast generation processes for the respective regions are rearranged to share TI as much as possible, thereby reducing a total scan time and allowing rapid capturing of a magnetic resonance image.

Figure 6:
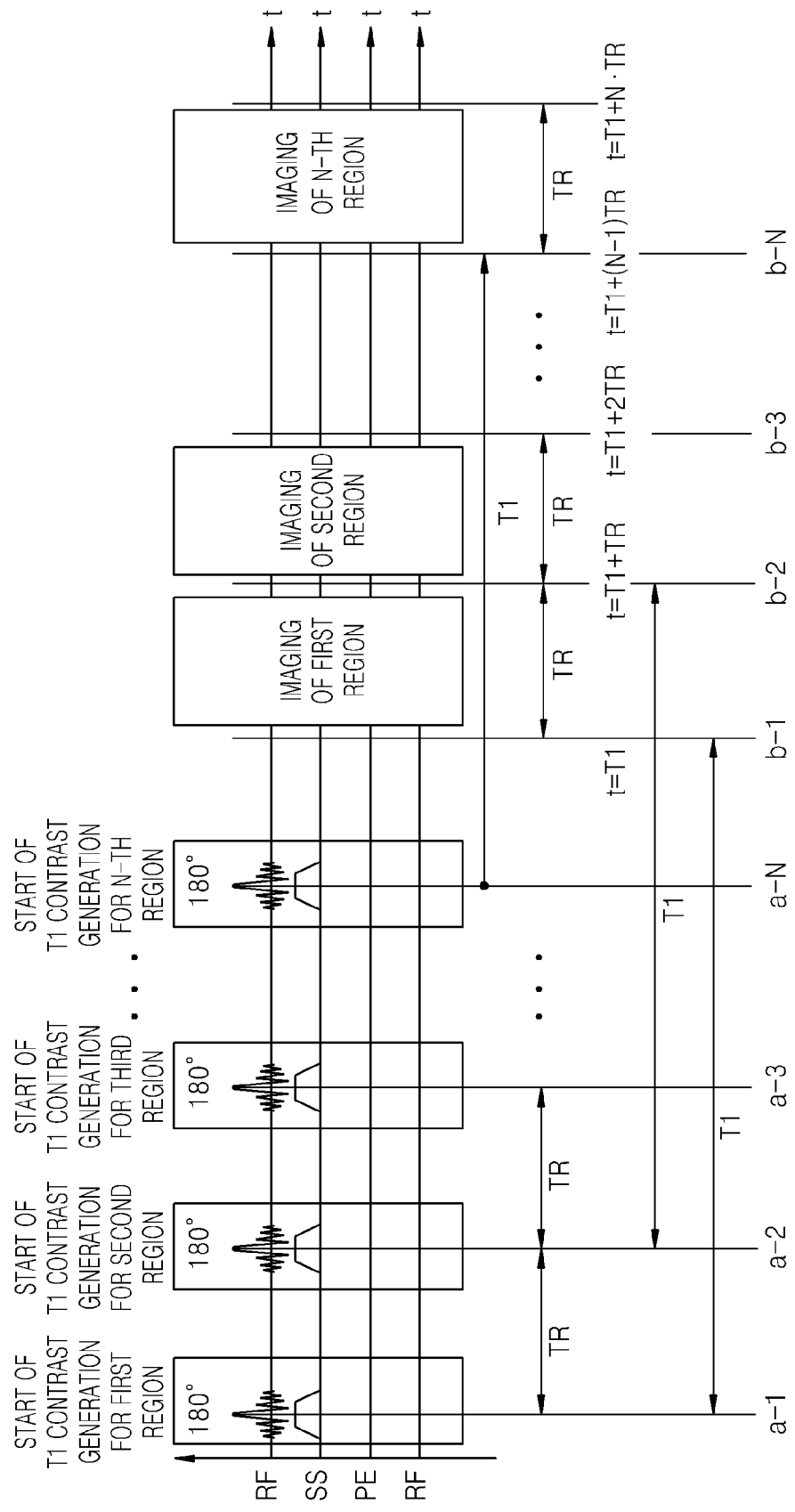
FIG. 6 is a diagram showing an example of a pulse sequence for obtaining T1 images with respect to a plurality of regions of an object in a technique for capturing a magnetic resonance image within a shorter time than in the example in FIG. 4.

FIG. 6 is a diagram of an example of a pulse sequence for obtaining T1 images with respect to a plurality of regions of an object in a technique for capturing a magnetic resonance image within a shorter time than in the example of FIG. 4. Hereinafter, the description provided with reference to FIG. 5 will be supplement using the pulse sequence shown in FIG. 6.

Referring to FIG. 6, a-1, a-2, a-3, . . . , a-N indicate start points of T1 contrast generation for the first through N-th regions, and b-1, b-2, b-3, . . . , b-N indicate start points of imaging for the first through N-th regions. It can be seen from FIG. 6 that a time consumed in T1 contrast generation for each region is a time corresponding to TI, and a time consumed in imaging for each region is a time corresponding to TR. A time consumed in obtaining a T1 image for each region is equal to a sum of TI and TR.

As can be seen from FIG. 6, the start point a-2 of T1 contrast generation for the second region occurs after the elapse of a predetermined time TR from the start point a-1 of T1 contrast generation for the first region and prior to the elapse of TI from the start point a-1. The start point a-2 occurs after the elapse of the predetermined time TR from the start point a-1. The predetermined time TR is shorter than TI.

In this disclosure, T1 contrast generation processes for the respective regions overlap to share TI, which is a time consumed in T1 contrast generation for each region of the object, as much as possible, thereby reducing a total scan time and allowing rapid capturing of a magnetic resonance image. The process of obtaining T1 images for the plurality of regions of the object shown in FIGS. 5 and 6 consumes a scan time expressed by Equation 2 above. When compared to the process of obtaining T1 images for the plurality of regions of the object shown in FIG. 4, the process shown in FIGS. 5 and 6 saves a scan time expressed by Equation 3 below.

$$\text{Saved Scan Time} = TI \times (N-1) \quad (3)$$

In the example of FIGS. 5 and 6, a total scan time for obtaining 10 images of a brain including gray matter and white matter in brain imaging is about 2 seconds, and a saved time compared to the example of FIG. 4 is about 9 seconds, that is, a time savings of about 82% is obtained.

Figure 7:
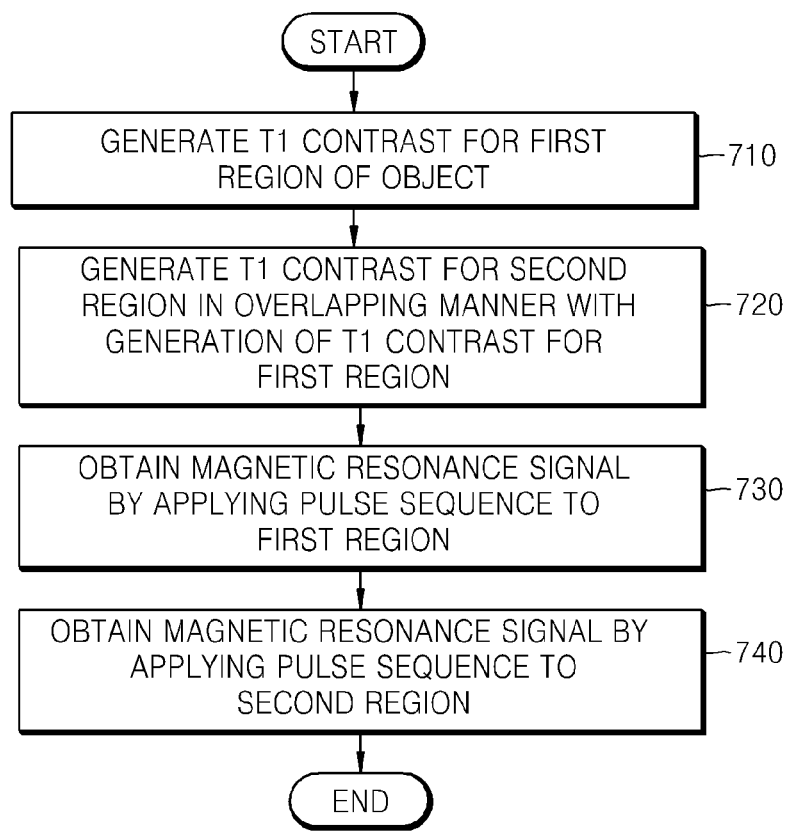
FIG. 7 is a flowchart showing an example of a method of capturing a magnetic resonance image within a shorter time than in the example in FIG. 4.

FIG. 7 is a flowchart showing an example of a method of capturing a magnetic resonance image within a shorter time than in the example of FIG. 4.

In operation 710, T1 contrast is generated for a first region of an object composed of different tissues. The object is divided into a plurality of regions to be imaged, and the plurality of regions may be different cross-sections of the object, or may be different subvolumes of the object. The object may be a particular part of the human body, and may be composed of at least two different tissues. Each tissue includes common atomic nuclei, such as hydrogen atomic nuclei, which exhibit a magnetic resonance phenomenon.

Once a 180° RF pulse is applied to the object for T1 contrast generation, the magnetization directions of hydrogen atomic nuclei of a first tissue and a second tissue in the object are rotated by 180°, and thereafter, upon the elapse of a predetermined time from the application of the RF pulse, the hydrogen atomic nuclei of the first tissue and the second tissue in the object are restored to their original magnetic moment directions. In this case, since there is a difference in the restoration speed and restoration time of the magnetic moment direction between the hydrogen atomic nuclei in the first tissue and the hydrogen atomic nuclei in the second tissue, T1 contrast is generated.

A spin lattice relaxation time, in other words, a T1 relaxation time, is a measurement indicating the degree of restoration of the magnetic moment direction of the hydrogen atomic nuclei over time. The spin lattice relaxation time refers to a time passing from application of an RF pulse to a restoration of a magnetic moment direction to 63.2% of the previous direction aligned by a static magnetic field when the RF pulse is applied to an object to rotate the magnetic moment direction by an angle corresponding to the applied RF pulse from the direction aligned by the static magnetic field. The spin lattice relaxation time refers to restoration of magnetization to a body axis direction (z-axis direction) of the object. Due to a T1 feature difference between hydrogen atomic nuclei included in respective tissues, T1 contrast is generated.

Once a predetermined time has elapsed after application of a 180° RF pulse to an object to generate T1 contrast, it may be regarded that T1 contrast is generated, and for example, upon the elapse of TI, it may be regarded that generation of T1 contrast is completed.

In step 720, T1 contrast for a second region of the object is generated in an overlapping manner with the generation of T1 contrast for the first region of the object. Generation of T1 contrast for the second region is the same as generation of T1 contrast for the first region described in step 710. That is, once an RF pulse considering the size of a gradient magnetic field existing in the second region is applied to the object, T1 contrast between different tissues of the second region is generated due to a T1 feature difference between hydrogen atomic nuclei of the different tissues of the second region. In particular, this disclosure overlaps T1 contrast generation for the second region with T1 contrast generation for the first region, thereby minimizing a time consumed in T1 contrast generation for a plurality of regions.

Overlapping T1 contrast generation for the first region with T1 contrast generation for the second region includes starting T1 contrast generation for the second region during T1 contrast generation for the first region. This may also be expressed as, during T1 contrast generation for the second region, starting a magnetic resonance signal obtaining process for imaging of the first region, which is performed immediately after completion of T1 contrast generation for the first region. In other words, a magnetic resonance signal obtaining process for imaging of the second region that is performed immediately after completion of T1 contrast generation for the second region starts when obtaining of the magnetic resonance signal for imaging of the first region is completed. In addition, T1 contrast generation for the second region may start after a delay of a predetermined time from the start of T1 contrast generation for the first region. The predetermined time may be a time corresponding to TR needed for imaging.

In step 730, a pulse sequence is applied to the first region of the object to obtain a magnetic resonance signal. More specifically, the control unit applies a drive signal to the RF coil driving unit 240, causing the RF coil driving unit 240 to apply a pulse sequence applying signal to the RF coil portion 226, causing the RF coil portion 226 to apply a pulse sequence to the object. The control unit 260 controls the pulse sequence for obtaining the magnetic resonance signal to be applied to the object upon completion of T1 contrast generation. For example, the control unit 260 may determine whether T1 contrast generation for the first region is completed based on whether TI has elapsed.

If the control unit 260 determines that T1 contrast generation for the first region is completed, e.g., that TI has elapsed, the control unit 260 controls the RF driving unit 240 to apply the pulse sequence applying signal to the RF coil portion 226, causing the RF coil portion 226 to apply the pulse sequence to the first region of the object. The pulse sequence may be any of various known pulse sequences, such as a spin echo pulse sequence or a gradient echo pulse sequence. The RF coil portion 226 receives magnetic resonance signals from different tissues of the object in response to the applied pulse sequence. The signal obtaining unit 250 obtains all magnetic resonance signals generated in respective tissue of the first region of the object, digitizes the magnetic resonance signals, and transmits the digitized magnetic resonance signals to the magnetic resonance image processing device 130, and the magnetic resonance image processing device 130 generates a magnetic resonance image using the digitized magnetic resonance signals and transmits the generated magnetic resonance image to the image display device 150.

In step 740, a pulse sequence is applied to the second region of the object to obtain a magnetic resonance signal. The process of obtaining a magnetic resonance signal by applying the pulse sequence to the second region is the same as the process of obtaining a magnetic resonance signal by applying the pulse sequence to the first region described in step 730. That is, if the control unit 260 determines that T1 contrast generation for the second region is completed, the control unit 260 controls the RF driving unit 240 to apply the pulse sequence applying signal to the RF coil portion 226, causing the RF coil portion 226 to apply the pulse sequence to the second region of the object. The RF coil portion 226 receives magnetic resonance signals from different tissues of the object in response to the applied pulse sequence. The signal obtaining unit 250 obtains all the magnetic resonance signals generated in the respective tissues of the second region of the object and digitizes the magnetic resonance signals and transmits the digitized magnetic resonance signals to the magnetic resonance image processing device 130.

The examples described above enable a time required for obtaining a magnetic resonance image to be reduced, and a magnetic resonance image enabling improved diagnosis of a disease or other abnormal condition to be provided.

The magnetic resonance image processing device 130, the image display device 150, the gradient driving unit 230, the RF driving unit 240, the signal obtaining unit 250, and the control unit 260 in FIGS. 1 and 2 described above that perform the operations illustrated in FIGS. 3-7 described above may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term 'processing device' may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and detail may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of generating a magnetic resonance image of an object, the method comprising:

generating a T1 contrast for a first region of the object composed of different tissues;

generating a T1 contrast for a second region of the object; and generating the magnetic resonance image of the object, based on the T1 contrast for the first region and the T1 contrast for the second region, wherein the generating of the T1 contrast for the first region and the generating of the T1 contrast for the second region overlap with each other, wherein a scan time for obtaining a T1 image for each of a plurality of regions of the object comprises an inversion time (TI) and a repetition time (TR), which is a time taken for imaging after the inversion time (TI), wherein the generating of the T1 contrast for the second region starts upon a time delay corresponding to the repetition time (TR) from a start of the generating of the T1 contrast for the first region, wherein the generating of the magnetic resonance image of the object starts upon a second time delay from a finish of respective generations of a T1 contrast for each of the plurality of regions, the second time delay corresponding to the repetition time.

2. The method of claim 1, further comprising:

obtaining a magnetic resonance signal from the first region by applying a pulse sequence with a first offset to the first region; and obtaining a magnetic resonance signal from the second region by applying the pulse sequence with a second offset to the second region.

3. The method of claim 2, wherein the obtaining of the magnetic resonance signal from the first region by applying the pulse sequence with the first offset to the first region starts during the generating of the T1 contrast for the second region.

4. The method of claim 2, wherein the obtaining of the magnetic resonance signal from the second region by applying the pulse sequence with the second offset to the second region starts upon completion of the obtaining of the magnetic resonance signal from the first region by applying the pulse sequence with the first offset to the first region.

5. The method of claim 1, further comprising generating a T1 contrast for a third region of the object;

wherein the generating of the T1 contrast for the second region and the generating of the T1 contrast for the third region overlap with each other.

6. The method of claim 5, further comprising:
obtaining a magnetic resonance signal from the first region by applying a pulse sequence with a first offset to the first region;
obtaining a magnetic resonance signal from the second region by applying the pulse sequence with a second offset to the second region; and
obtaining a magnetic resonance signal from the third region by applying the pulse sequence with a third offset to the third region.

7. The method of claim 1, wherein the first region and the second region are different cross-sections of the object.

8. The method of claim 1, wherein the first region and the second region are different subvolumes of the object.

9. A non-transitory computer-readable storage medium storing a program for controlling a computer to control an apparatus for generating a magnetic resonance image to perform the method of claim 1.

10. An apparatus for capturing a magnetic resonance image, the apparatus comprising:
a radio-frequency (RF) coil portion configured to apply an RF pulse to a first region of an object, composed of different tissues, for generating a T1 contrast for the first region, and to apply the pulse to a second region of the object for generating a T1 contrast for the second region; and
a control unit configured to determine a time point at which the RF pulse with a first offset is applied to the first region for the generating of the T1 contrast for the first region and a time point at which the RF pulse with a second offset is applied to the second region for the generating of the T1 contrast for the second region so that the generating of the T1 contrast for the first region and the generating of the T1 contrast for the second region overlap with each other,
wherein a scan time for obtaining a T1 image for each of a plurality of regions of the object comprises an inversion time (TI) and a repetition time (TR), which is a time taken for imaging after the inversion time (TI), and
wherein the control unit is further configured to:
determine a time point at which the RF pulse with the second offset is applied to the second region to be a time point delayed by a time corresponding to the repetition time (TR), from a time point at which the RF pulse with the first offset is applied to the first region; and
start generating the magnetic resonance image of the object upon a time delay after respective generations of a T1 contrast for each of the plurality of regions, the time delay corresponding to the repetition time.

11. The apparatus of claim 10, wherein the RF coil portion is further configured to apply respective pulse sequences with different offsets, for obtaining a magnetic resonance signal, to the first region and to the second region; and
the apparatus further comprises a signal obtaining unit configured to obtain a magnetic resonance signal from the first region in response to a pulse sequence with the first offset applied to the first region, and a magnetic resonance signal from the second region in response to the pulse sequence with the second offset applied to the second region.

12. The apparatus of claim 11, wherein the control unit is further configured to start the obtaining of the magnetic resonance signal from the first region during the generating of the T1 contrast for the second region.

13. The apparatus of claim 11, wherein the control unit is further configured to start the obtaining of the magnetic resonance signal from the second region upon completion of the obtaining of the magnetic resonance signal from the first region.

14. The apparatus of claim 10, wherein the RF coil portion is further configured to apply the RF pulse with a third offset to a third region of the object for generating a T1 contrast for the third region.

15. The apparatus of claim 14, wherein the RF coil portion is further configured to apply respective pulse sequences with different offsets, for obtaining a magnetic resonance signal, to the first region, to the second region, and to the third region; and
the apparatus further comprises a signal obtaining unit configured to obtain a magnetic resonance signal from the first region in response to a pulse sequence with a first offset applied to the first region, a magnetic resonance signal from the second region in response to the pulse sequence with a second offset applied to the second region, and a magnetic resonance signal from the third region in response to the pulse sequence with a third offset applied to the third region.

16. The apparatus of claim 10, wherein the first region and the second region are different cross-sections of the object.

17. The apparatus of claim 10, wherein the first region and the second region are different subvolumes of the object.

18. An apparatus for generating a magnetic resonance image of an object, the apparatus comprising:
one or more processors configured to:
generate a T1 contrast for a first region of the object composed of different tissues;
generate a TI contrast for a second region of the object after a time delay corresponding to a repetition time from a start of the generating of the T1 contrast for the first region; and
generating the magnetic resonance image of the object, based on the T1 contrast for the first region and the T1 contrast for the second region, the generating of the magnetic resonance image of the object starting upon a second time delay from a finish of respective generations of a T1 contrast for each of a plurality of regions, and the second time delay corresponding to the repetition time, wherein
the generating of the T1 contrast for the first region and the generating of the contrast for the second region overlap with each other, and
a time for obtaining a T1 image for each of a plurality of regions of the object comprises an inversion time and the repetition time, which is a time taken for imaging after the inversion time.

19. The apparatus of claim 18, wherein a total time for the generating of the magnetic resonance image of the object amounts to a sum of the inversion time and a multiplying result, the multiplying result being obtained from multiplying the repetition time by a number of the plurality of regions.

* * * * *